United States Patent [19]

Feinmann

[11] Patent Number: 4,600,386
[45] Date of Patent: Jul. 15, 1986

[54] APPARATUS FOR THE PRODUCTION OF SMALL DENTAL PROSTHESES

[76] Inventor: Paul B. Feinmann, 18, chemin Barbey, 1292 - Chambesy - Canton of Geneva, Switzerland

[21] Appl. No.: 744,217

[22] Filed: Jun. 13, 1985

[30] Foreign Application Priority Data

Aug. 14, 1984 [CH] Switzerland .................. 3.896/84

[51] Int. Cl.⁴ .............................................. A61C 11/00
[52] U.S. Cl. .......................................... 433/60; 433/54
[58] Field of Search ................. 433/60, 54, 55, 56, 433/57, 58, 59, 61, 62, 63, 64, 65, 66, 67

[56] References Cited

U.S. PATENT DOCUMENTS

| | | | |
|---|---|---|---|
| 659,871 | 10/1900 | Lewis | 433/58 |
| 2,911,722 | 11/1959 | Benfield et al. | 433/60 |
| 4,155,163 | 5/1979 | Schwartz | 433/56 |
| 4,439,151 | 3/1984 | Whelan | 433/60 |

*Primary Examiner*—John J. Wilson
*Attorney, Agent, or Firm*—Silverman, Cass & Singer, Ltd.

[57] ABSTRACT

A quadrant impression carrier is provided with ribs bearing on the edge of a through aperture of corresponding shape provided in an occlusion table of an articulator. The impression carrier is thus hooked in the opening, which enables the articulator to be used for the production of small prostheses whereas, originally, such apparatus was provided for the production of complete prostheses, the small prostheses normally being executed on occlusors the arms of which are merely articulated and do not have several degrees of freedom in their movements.

3 Claims, 3 Drawing Figures

APPARATUS FOR THE PRODUCTION OF SMALL DENTAL PROSTHESES

BACKGROUND OF THE INVENTION (a) Field of the Invention

The present invention relates to apparatus for the production of small dental prostheses by means of quadrant impression carriers.

(b) Description of the Prior Art

Quadrant impression carriers are intended to allow the production of small prostheses, of one to four teeth at the maximum. They allow an impression to be taken with closed mouth, without producing any risk of vomiting by the patient.

The impression thus achieved, utilising a silicone polyether or polysulfide impression paste, for example, serves for the production of a plaster cast which is then used on an occlusor to enable the production of the artificial tooth or teeth of the prosthesis.

The occlusor, in contrast to an articulator, has a movable arm which can effect only an oscillatory movement about its axis while the movable arm of an articulator has several degrees of freedom.

The use of an occlusor presents the drawback of not enabling the actual movements of the lower jaw to be reproduced, movements which comprise not only a rotation but also a lateral displacement (movement of Bennett).

Hence the prostheses produced utilising such occlusors require adjustment in the mouth, which has to be effected by the dentist, which can be complex and must be much more important when the material from which the prosthesis is made is less ductile, which is especially the case with the porcelains which are becoming more and more frequently used, and which do not adjust themselves during wear.

SUMMARY OF THE INVENTION

The object of the present invention is to remove the foregoing drawbacks while permitting use for the production of such small prostheses, in place of the above mentioned occlusors, of articulators which are more sophisticated and enable the achievement of prostheses which are more elaborate, such articulators initially being intended for the production of complete prostheses and not of small prostheses obtained by means of quadrant impression carriers.

This object is achieved by the fact that the apparatus according to the invention comprises an articulator the arm of which has several degrees of freedom, provided with an occlusion table pierced with at least one opening having a shape corresponding to that of a quadrant impression carrier, the latter being provided with at least two outward protrusions intended to bear on the table for the purpose of maintaining the impression carrier hooked in the opening.

The various features of the invention will be apparent from the following description, drawings and claims, the scope of the invention not being limited to the drawings themselves as the drawings are only for the purpose of illustrating ways in which the principles of the invention can be applied. Other embodiments of the invention utilising the same or equivalent principles may be used and structural changes may be made as desired by those skilled in the art without departing from the present invention and the purview of the appended claims.

DESCRIPTION OF THE PREFERRED EMBODIMENTS

Figure 1:
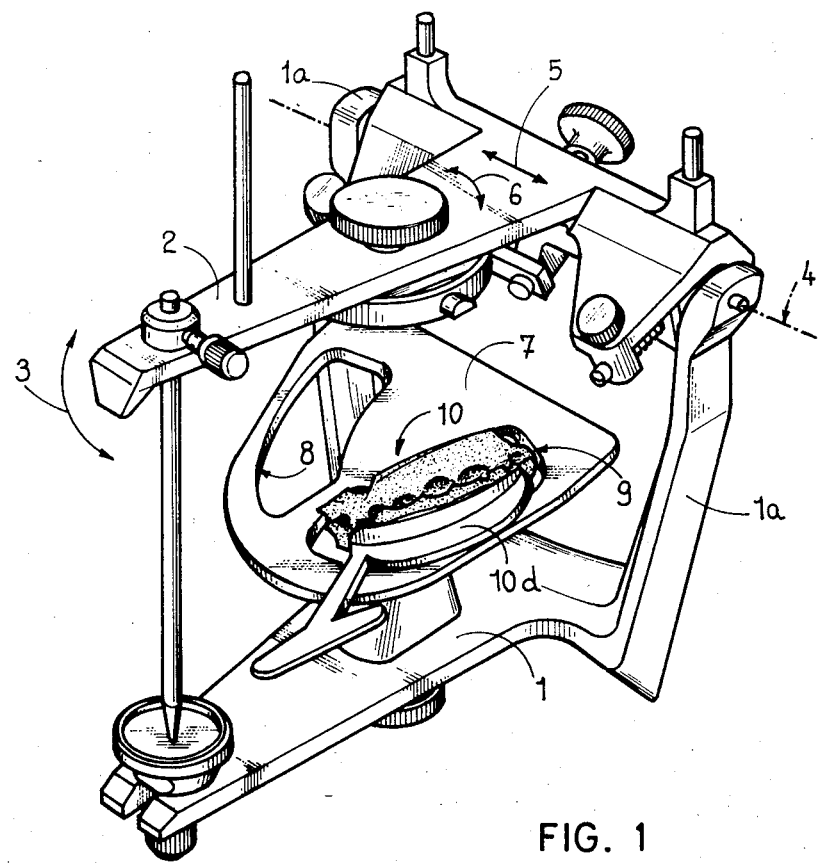
FIG. 1 is a perspective view of an articulator the table of occlusion of which carries a quadrant impression carrier.

The articulator illustrated in FIG. 1 comprises a frame 1 having a stirrup shaped portion the two arms of which, designated by 1a, carry an articulated arm 2. The mechanism for sustaining this arm, known per se, is arranged in such manner as to allow the arm to oscillate in the direction of the arrow 3, about an axis designated by reference 4, to effect translatory movement in the direction of the arrow 5, parallel to the axis 4, and rotate by a small amount in the direction of the arrow 6, that is to say about an axis which is perpendicular to the axis 4.

The occlusion table of this articulator, designated by reference 7, is provided with two shaped apertures 8 and 9 respectively adapted to receive right and left quadrant impression carriers, such as the left impression carrier, designated by reference 10, which is shown in position in the opening 9.

Figure 2:
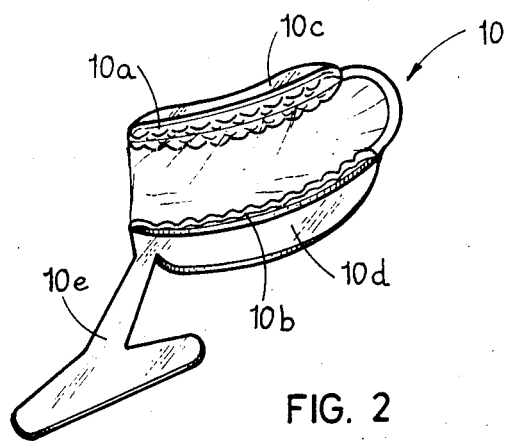
FIG. 2 is a perspective view of this impression carrier, to a larger scale.
Figure 3:
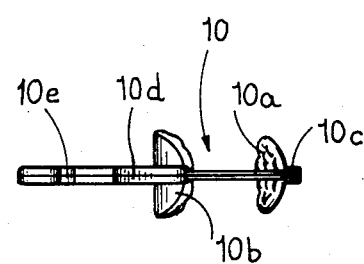
FIG. 3 is an elevational view, seen from one end, of this impression carrier.

The impression carrier 10, shown in detail in FIGS. 2 and 3, has two arms 10a and 10b provided respectively with two plane ribs 10c and 10d, the latter being prolongated by a handle 10e situated in a same plane. The ribs 10c and 10d are adapted to bear on the edge of the opening 9 of the table 7 in such manner as to maintain the impression carrier hooked in the corresponding table aperture. As a modification, these ribs could be replaced by any other protrusions performing the same function.

Owing to this arrangement the articulator, the arm of which has several degrees of freedom in its movements, is usable for the production of small prostheses having one to four teeth, which are thus so far completed in their manufacture as complete prostheses would be and which, consequently, require a minimum of adjustment to be effected in the mouth of the patient by the dentist, as with the complete prostheses.

As a further modification, there can be provided the case where the table 7 presents only one aperture, which will permit the articulation of not only impressions of lateral quadrants, but also "bite" impressions of the front portion of the jaw, that is to say of the incisors.

We claim:

1. Apparatus for producing small dental prostheses with quadrant impression carriers comprising, an articulator, the articulator including a movable arm and an occlusion table, the table having at least one opening provided therein, a quadrant impression carrier removably position in said opening, said quadrant impression carrier having at least two outwardly extending arms formed thereon to bear on said table to maintain the quadrant impression carrier hooked in said opening.

2. Apparatus as claimed in claim 1, in which there are two openings provided in said occlusion table, one of said openings adapted to receive a right quadrant impression carrier and the other of said openings adapted to receive a left quadrant impression carrier.

3. Apparatus as claimed in claim 1, in which each arm of the quandrant impression carrier has an outer rib intended to bear on the edge of the opening of the occlusion table.

* * * * *